United States Patent [19]

Bernier

[11] 4,296,358

[45] Oct. 20, 1981

[54] HIGH-VOLTAGE SPARK SOURCE

[75] Inventor: John A. Bernier, Lexington, Mass.

[73] Assignee: Fisher Scientific Company, Pittsburgh, Pa.

[21] Appl. No.: 62,244

[22] Filed: Jul. 30, 1979

[51] Int. Cl.³ .............................................. H05B 7/20
[52] U.S. Cl. ............................... 315/241 R; 315/205; 315/209 CD; 315/240; 315/243
[58] Field of Search ................ 315/205, 209 CD, 240, 315/241 R, 242-245; 320/1; 356/313

[56] References Cited

U.S. PATENT DOCUMENTS

| | | | |
|---|---|---|---|
| 3,749,975 | 7/1973 | Walters | 315/241 R |
| 3,973,167 | 8/1976 | Walters et al. | 315/240 X |
| 4,055,783 | 10/1977 | Walters et al. | 315/244 X |

OTHER PUBLICATIONS

Rudnevskii et al., *Pulse-Arc Generator as Light Source for Spectral Analysis*, Translated from Zhurnal Prikladnoi Spektroskopii, vol. 17, No. 4, pp. 738-742, Oct. 1972.

*Primary Examiner*—Eugene R. La Roche

[57] ABSTRACT

A spark source circuit has a discharge circuit including reactive means connected in circuit between a capacitor and an analytical spark gap and switching means for effectively removing the capacitor from the discharge circuit after an initial flow of current through the spark gap so that the current flow through the spark gap is essentially unidirectional. At the start of the capacitor discharge, the discharge circuit is essentially of the classical RLC oscillatory discharge type; and the switching action converts the discharge circuit to essentially a classical RL discharge type circuit for the remainder of the spark discharge. The circuit is simple and efficient, permits use of ceramic capacitors, and may be housed in a sealed enclosure.

18 Claims, 7 Drawing Figures

FIG 2
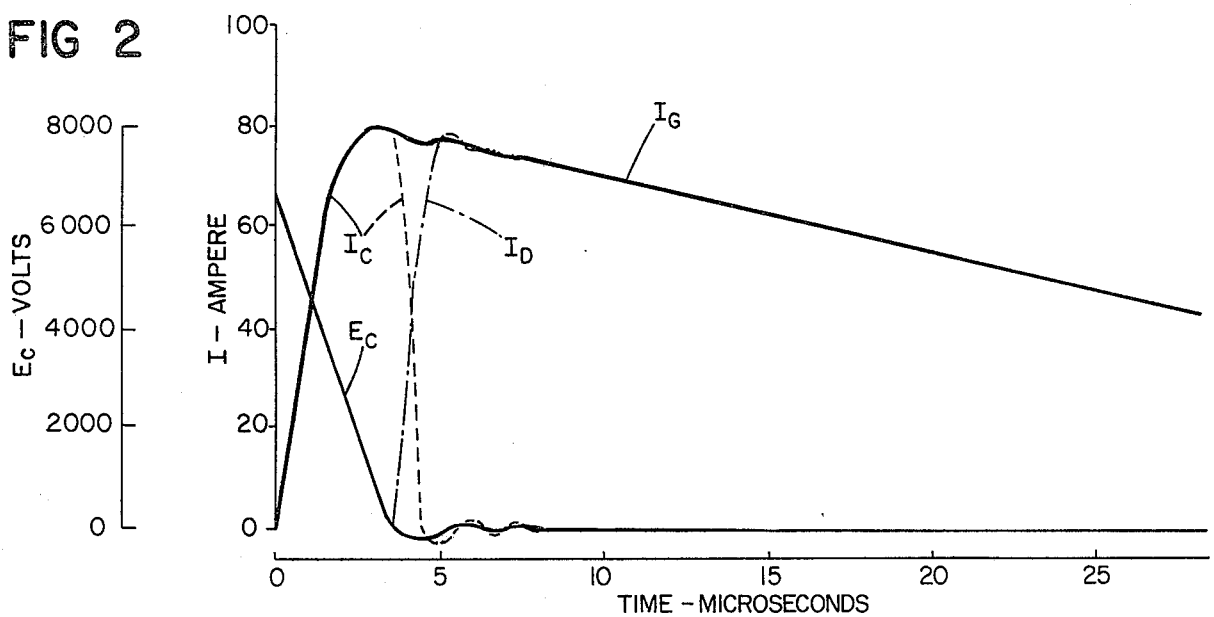
FIG 3
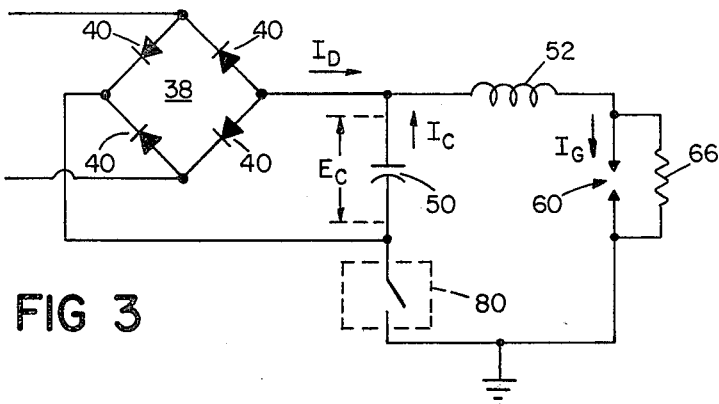
FIG 4
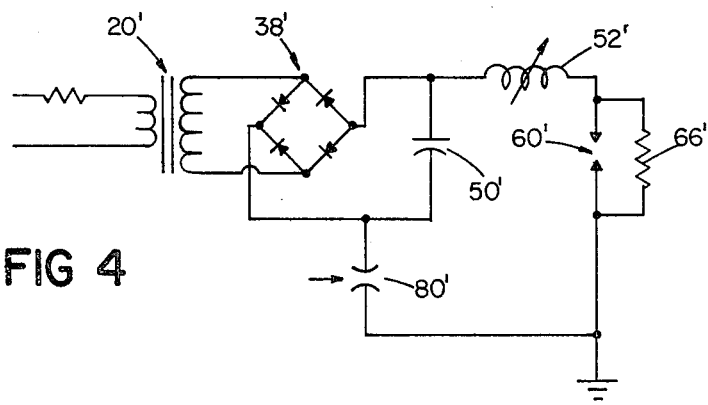
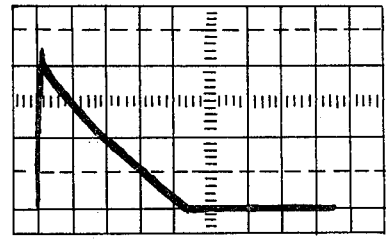
FIG 5A
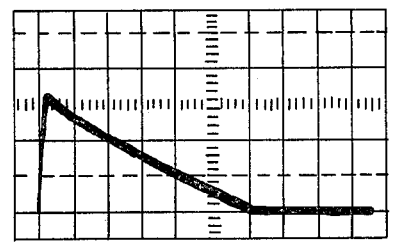
FIG 5B
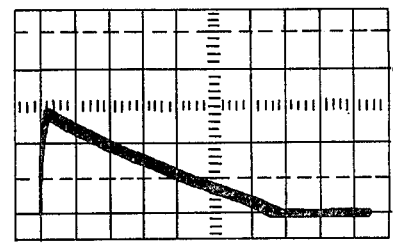
FIG 5C

HIGH-VOLTAGE SPARK SOURCE

This invention relates to spectroscopic analysis and more particularly to high-voltage spark sources for use in spectroscopic analysis.

In spectroscopic analytical techniques using high voltage spark sources, material from the sample to be analyzed is introduced into an analytical spark gap and spark discharges across the spark gap vaporize some of the sample material. The vaporized sample material may be excited to spectroemissive energy levels sufficient to emit reliably detectable radiation characteristic of all the elements in the sample by the spark discharges themselves or by supplemental excitation. The resulting emitted radiations are analyzed spectroscopically to determine the composition of the sample material. Such techniques are especially valuable in analyzing metals and metal alloys. Spark sources of these general types are described in Walters, "Historical Advances in Spark Emission Spectroscopy", Applied Spectroscopy, 23, 317 (1969); Walters, "An Adjustable-Waveform High-Voltage Spark Source for Optical Emission Spectrometry", Analytical Chemistry, 40, 1672 (1968); Coleman et al, "An Electronic, Adjustable-Waveform Spark Source for Basic and Applied Emission Spectrometry", Spectrochimica Acta, 31B, 547 (1976); and in U.S. Pat. Nos. 3,749,975 and 3,973,167.

In accordance with one feature of the invention, a spark source circuit has a discharge circuit including reactive means connected in circuit between a capacitor and an analytical spark gap and switching means for essentially removing the capacitor from the discharge circuit after a brief initial flow of current through the spark gap so that the current flow through the spark gap is essentially unidirectional. At the start of the capacitor discharge, the discharge circuit is essentially of the classical RLC oscillatory discharge type; and the switching action converts the discharge circuit to essentially a classical RL discharge type circuit for the remainder of the spark discharge. The waveform of the current through the spark gap is a substantially nonoscillatory triangularly-shaped pulse which rises rapidly towards peak and then gradually falls, and has a typical duration of about 100 microseconds.

In preferred embodiments, the switching means is rectifier circuitry connected directly to the capacitor for charging the capacitor to a high voltage and the rectifier circuitry, in response to the voltage on the capacitor reaching zero volts (which in preferred circuits occurs in less than 5 microseconds), conducts and shunts flow of the current around the capacitor for the remainder of the spark discharge. The circuit is simple and efficient, permits use of ceramic capacitors, and may be housed in a sealed enclosure. Among the advantages are reduced heating and reduced radio frequency emission.

While a variety of spark initiating arrangements may be used, including devices such as blower gaps and thyratrons, in accordance with another feature of the invention, in preferred embodiments, a long-life, low trigger power switch which includes a stack of semiconductor switch devices connected in series between the capacitor and the spark gap is employed. In response to a triggering signal, the semiconductor switch devices are initially switched serially into conduction followed by an essentially concurrent switching of the remaining semiconductor switch devices into conduction, effectively closing the switch and transferring the voltage on the charged capacitor to the spark gap to initiate the spark discharge. In a particular embodiment, each semiconductor switch stage includes a controlled rectifier and voltage distributing means, and the concurrent switching action is responsive to the voltage across each nonconducting switch stage exceeding a predetermined value. Also, in that particular embodiment, the spark initiating switch is triggered as a function of the voltage on the capacitor in an arrangement which provides uniform waveform characteristics of successive spark discharges through the analytical spark gap.

Other features and advantages of the invention will be seen as the following description of particular embodiments progresses, in conjunction with the drawings, in which:

FIG. 2 is a graph indicating voltage and current conditions in the circuit of FIG. 1, a simplified diagram of that circuit being shown in FIG. 3;

FIG. 4 is a schematic circuit diagram of another embodiment of a spark source in accordance with the invention; and FIGS. 5A, B, and C are a set of waveform diagrams showing the manner in which the spark gap current waveform may be changed by changing the inductance value.

DESCRIPTION OF PARTICULAR EMBODIMENTS

Figure 1:
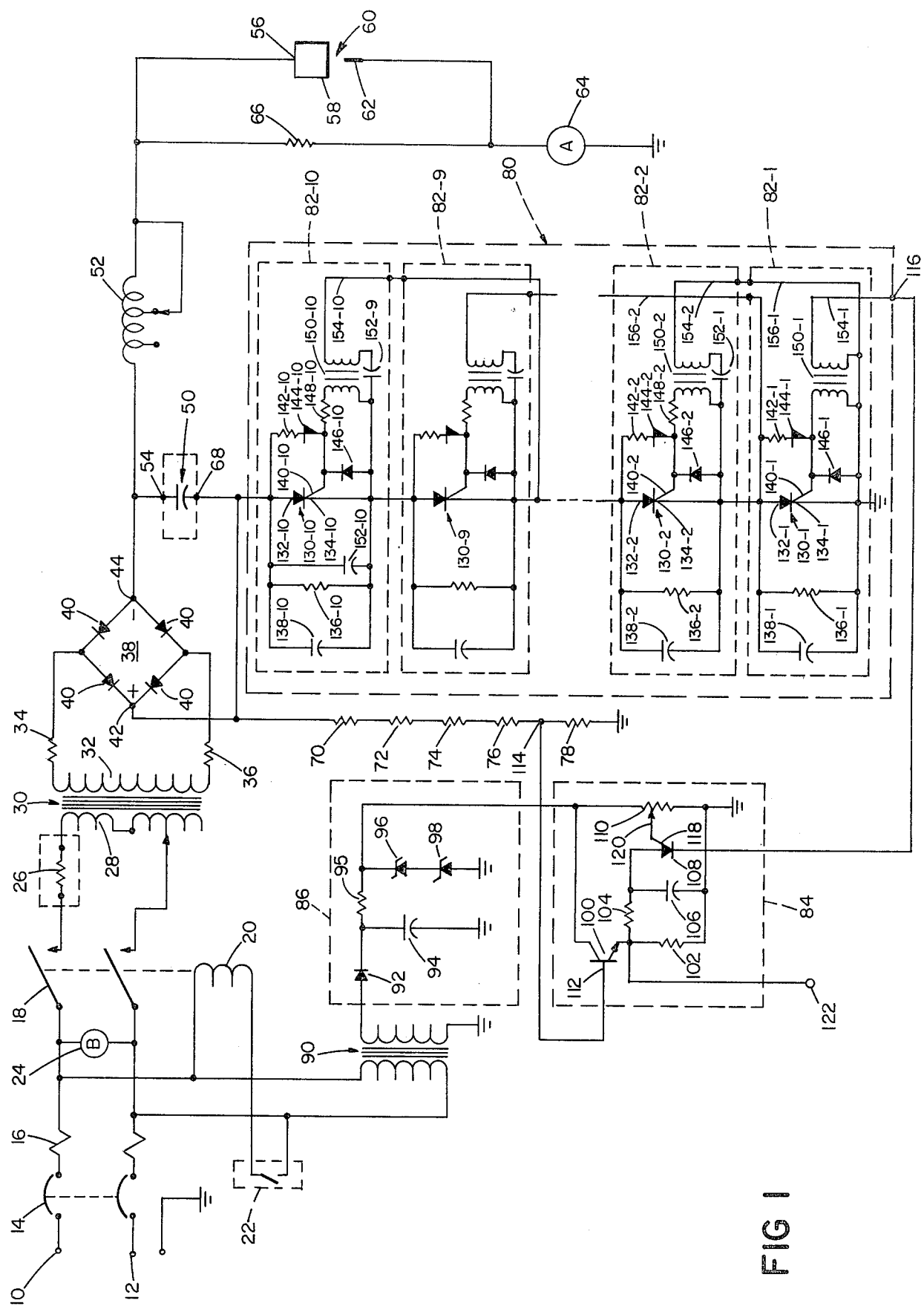
FIG. 1 is a schematic circuit diagram of a spark source in accordance with the invention.

The analytical spark source circuit shown in FIG. 1 has supply terminals 10, 12 connected through circuit breaker 14 and fuses 16 to contacts 18 of start relay 20 that is controlled by switch 22. Blower 24 is energized when circuit breaker 14 is closed. Contacts 18 are connected through resistor 26 to the primary winding 28 of transformer 30. The secondary winding 32 of transformer 30 is connected through resistors 34, 36 to rectifier circuit 38 that includes four high voltage diodes 40.

Connected between plus terminal 42 and negative terminal 44 of the rectifier circuit 38 is storage capacitor 50 which is composed of 75 ceramic capacitors in a series parallel arrangement of five groups of fifteen capacitors each to provide a capacitance value of 0.03 microfareds and a voltage rating of fifteen kilovolts. Adjustable air core inductor 52 is connected between the negative terminal 54 of capacitor 50 and electrode 56 of the analytical spark gap 60 which receives sample material 58 and through which argon gas is flowed. Tungsten counter electrode 62 of spark gap 60 is connected through RF ammeter 64 to ground. High voltage resistor 66 is connected across the analytical spark gap 60.

Connected to the positive terminal 68 of capacitor 50 is a voltage divider network or resistors 70, 72, 74, 76, and 78 and a high voltage switch 80 that consists of ten semiconductor switch stages 82-1 - 82-10 that are connected in series between the positive terminal 68 of capacitor 50 and ground.

The circuit also includes a trigger circuit 84 and a power supply 86 that provides a regulated 25 volt supply to trigger circuit 84. Power supply 86 includes isolation transformer 90, diode 92, capacitor 94, and two zener diodes 96, 98. The trigger circuit includes transistor 100, resistors 102, 104, capacitor 106, programmable unijunction transistor 108 and potentiometer 110. The base 112 of transistor 110 is connected to the tap 114 between resistors 76 and 78. The output voltage from transistor 100 charges capacitor 106 through resistor 104. The positive terminal of capacitor 106 is connected to the anode of PUT 108, the cathode of PUT 108 is connected to the control input 116 of electronic switch 80, and the gate terminal 118 of PUT 108 is connected to the slider 120 of potentiometer 110. Test point 122 provides convenient monitoring of the trigger circuit.

Electronic switch 80, as indicated above, includes ten semiconductor switch stages 82 connected in series. Each switch stage 82 is mounted on a separate heat sink and includes a controlled rectifier (SCR) 130 with the anode 132 of each stage connected to the cathode 134 of the SCR of the next stage. Connected across anode and cathode of each SCR is a resistor 136 and a capacitor 138, resistor 136 providing equivoltage distribution and capacitor 138 providing capacitance balancing. Connected between the anode of each SCR and its gate 140 is a series circuit of resistor 142 and break-over diode 144. A reverse voltage protection diode 146 is connected between each gate 140 and cathode 134. Also connected to gate 140 of each SCR via current limiting resistor 148 is the secondary winding of a pulse transformer 150. A capacitor 152 is connected in parallel with each capacitor 138, stages 82-1 - 82-9 having the capacitor 152 connected between the pulse transformer primary winding of that stage and its SCR cathode 134. Each semiconductor switch stage 82 has a trigger pulse input line 154 and an output line 156 that couples a trigger signal to the next stage. The first stage (stage 82-1) of switch 80 has its trigger input 154-1 connected to trigger terminal 116 and a trigger output on line 156-1. Switch stages 82-3 - 82-8 are identical to stages 82-2 and 82-9.

Set out in the following table are values of components employed in the circuit of FIG. 1. Those skilled in the art will understand that the values of various components can be varied widely to suit various conditions:

| Component | Reference No. | Value |
| --- | --- | --- |
| Resistor | 26 | 10 ohms - 200W |
| Transformer | 30 | 120V/6000V |
| Resistor | 34 | 3K - 25W |
| Resistor | 36 | 3K - 25W |
| Diode | 40 | FMC EFLH 20 |
| Capacitor | 50 | 0.03 microfared (75 Sprague 30GA 0.01 μf capacitors) |
| Inductor | 52 | 0-560 microhenries |
| Resistor | 66 | 54 ohms - 100W |
| Resistor | 70, 72, 74, 76 | 2.2 M - 2W |
| Resistor | 78 | 27K - ½W |
| Transformer | 90 | 120V/120V |
| Diode | 92 | 1N4007 |
| Capacitor | 94 | 4 microfared |
| Resistor | 95 | 15K - 2W |
| Zener Diode | 96, 98 | 1N5243B |
| Transistor | 100 | 2N6014 |
| Resistor | 102, 104 | 10K - ½W |
| Capacitor | 106 | 0.01 microfared |
| Transistor | 108 | 2N6116 |
| Potentiometer | 110 | 100K |
| SCR | 130 | FMC 40C100 |
| Resistor | 136 | 100K - 2W |
| Capacitor | 138 | 0.01 microfared |
| Resistor | 142 | 1K - ½W |
| Diode | 144 | Brown Boverie BOD1-10 |
| Diode | 146 | 1N4007 |
| Resistor | 148 | 2.2K - ½W |
| Transformer | 150 | 1:1 |
| Capacitor | 152 | 0.01 microfared |

In operation, closure of circuit breaker 14 applies power to start relay contacts 18, blower 24, and power supply 86. Closure of control switch 22 energizes relay 20 to close contacts 18, applying power through step-up transformer 30 to rectifier network 38 to charge capacitor 50. The voltage at the positive terminal 68 of capacitor 50 rises as the rectified line voltage increases from the zero voltage crossing. The voltage is monitored by the voltage divider network of resistors 70-78 and the voltage at tap 114 is applied to the base of transistor 100 to charge capacitor 106. When the voltage across capacitor 106 exceeds the voltage applied to gate 118 of PUT 108 by potentiometer 110, transistor 108 is fired and capacitor 106 discharges through that transistor to apply a trigger pulse to terminal 116 of electronic switch 80.

The trigger pulse applied at terminal 116 is coupled by transformer 150-1 to fire SCR 130-1, i.e., effectively short circuiting anode 132-1 to cathode 134-1. Before firing, commutating capacitor 152-1 has been charged to the voltage across SCR 130-1. When SCR 130-1 fires, capacitor 152-1 is discharged through the primary of transformer 150-2, inducing a current pulse on the secondary of transformer 150-2 that fires SCR 130-2. As this serial triggering process is repeated the voltage across each of the remaining unfired SCR's increases. When the voltage exceeds the voltage limit of break-over diodes 144, the break-over diodes conduct and pass current pulses which concurrently fire the remaining nonconducting SCR's. This triggering action effectively closes switch 80, connecting the plus terminal 68 of charged capacitor 50 to ground and transferring the voltage of charged capacitor 50 to spark gap 60. Gap 60 breaks down, completing a circuit for capacitor 50 to discharge through inductor 52 and gap 60.

A waveform diagram of currents and voltage during the spark discharge is shown in FIG. 2 (with these parameters indicated in FIG. 3—a simplified diagram of the circuit shown in FIG. 1). Current flow $I_C$ from charged capacitor 50 commences in response to breakdown of gap 60 and flows through gap 60, rising rapidly and reaching a peak of about eighty amperes approximately 3.5 microseconds after switch 80 is closed. The voltage $E_C$ on capacitor 50 concurrently falls from its initial value of about 6700 volts and reaches zero volts approximately 3.5 microseconds after switch 80 has been closed. At that time, and in response to that capacitor voltage, rectifier diodes 40 conduct (the diode current being indicated at $I_D$) and essentially prevent the voltage on capacitor 50 from swinging negative. The conduction of diodes 40 provides a current flow path around capacitor 50, effectively shunting capacitor 50 so that the capacitor current $I_C$ falls and the spark gap discharge circuit is converted from a classical RLC oscillatory circuit to a classical RL circuit in which the gap current $I_G$ (supplied by inductor 52) falls to zero in about 100 microseconds. The circuit thus provides a spark discharge in the form of a substantially nonoscillatory triangularly shaped current pulse that has a rapid rise and a gradual fall.

The specific current waveform across spark gap 50 depends on circuit parameters, such as the trigger voltage, the values of capacitor 50 and of inductor 52, residual impedances in series with the diodes 40 and distributed inductances of the connecting leads for example, which may be changed to provide different spark gap current pulses as desired. In a typical analysis cycle, the spark source circuitry of FIG. 1 generates 240 sparks per second for a period of thirty seconds. The spark source circuitry operates normally (without harm) with the spark stand short circuited. Also, should sample 58 be left out of the spark stand, there will be no spark but capacitor 50 will discharge through resistor 66 in response to each trigger signal. These features provide increased circuit reliability.

Shown in FIG. 4 is a spark gap circuit similar to the FIG. 1 circuit that uses a conventional control blower gap 80' as the discharge triggering switch. The waveforms shown in FIGS. 5A, 5B, and 5C are oscillograms of the gap current waveform in the circuit of FIG. 4 with a capacitor 50' of 0.03 microfared value and an inductor 52' with 40 turns (FIG. 5A); 70 turns (FIG. 5B); and 80 turns (FIG. 5C) respectively. The oscillogram of FIG. 5A shows a spark gap current pulse with a peak amplitude of about 90 amperes and a duration of about 80 microseconds; the oscillogram of FIG. 5B shows a spark gap current pulse with a peak amplitude of about 65 amperes and a duration of about 120 microseconds; and the oscillogram of FIG. 5C shows a spark gap current with a peak amplitude of about 55 amperes and a duration of about 130 microseconds. Other waveform variations can be obtained by changing other circuit parameters.

While particular embodiments of the invention have been shown and described, other embodiments will be apparent to those skilled in the art, and therefore it is not intended that the invention be limited to the disclosed embodiment or to details thereof and departures may be made therefrom within the spirit and scope of the invention.

What is claimed is:

1. A spark source for spectrochemical analysis comprising
   a spark gap for receiving a sample to be analyzed,
   a storage capacitor,
   a discharge circuit including reactive means connected in circuit between said capacitor and said spark gap,
   discharge control means for discharging said capacitor through said spark gap, and
   switching means for effectively removing said capacitor from said discharge circuit after a brief initial interval of current flow through said spark gap so that the current flow through said spark gap is essential unidirectional.

2. A high voltage spark source comprising:
   an analytical spark gap having a grounded electrode and an ungrounded electrode,
   a capacitor adapted to be discharged across said spark gap,
   said capacitor having positive and negative terminals adapted to be charged positively and negatively,
   a discharge circuit connected between said capacitor and said spark gap,
   said discharge circuit including an inductive element connected in series with said spark gap and discharge control means, and
   switching means connected across said capacitor, said switching means being conductive after an initial flow of the capacitor discharge current whereby said switching means converts said discharge circuit from essentially an RLC circuit to essentially an RL circuit.

3. The spark source of claim 2 wherein said inductive element has sufficient inductance to maintain a unidirectional current flow through said spark gap after said initial flow of said capacitor discharge current.

4. The spark source of either claim 1 or 2 wherein said switching means includes rectifier circuitry connected to said capacitor for charging said capacitor to a high voltage, said rectifier circuitry shunting flow of current around said capacitor after said initial interval.

5. The spark source of claim 4 wherein said rectifier circuitry is connected directly to said capacitor.

6. A spark source for spectrochemical analysis comprising
   a spark gap for receiving a sample to be analyzed,
   a storage capacitor,
   reactive means connected in circuit between said capacitor and said spark gap, and
   discharge control means for discharging said capacitor through said spark gap including a plurality of semiconductor switch devices connected in series between said capacitor and said spark gap, and each said semiconductor switch device includes a controlled rectifier, voltage distributing means, and voltage breakdown means responsive to the voltage across the device for switching said controlled rectifier into conduction.

7. The spark source of either claim 1 or 2 wherein said discharge control means is responsive to voltage on said capacitor.

8. The spark source of claim 1 wherein said discharge control means includes a semiconductor switch.

9. The spark source of claim 8 wherein said semiconductor switch includes a plurality of semiconductor switch devices connected in series between said capacitor and said spark gap.

10. The spark source of claim 9 and further including means responsive to a triggering signal for initially serially switching said semiconductor switch devices into conduction followed by an essentially concurrent switching of a plurality of semiconductor devices of said switch into conduction.

11. A spark source of claim 10 wherein said concurrent switching is responsive to the voltage across individual semiconductor switch devices.

12. The spark source of claim 9 wherein each said semiconductor switch device includes a controlled rectifier, voltage distributing means, and voltage breakdown means responsive to the voltage across the device for switching said controlled rectifier into conduction.

13. The spark source of claim 12 wherein each said controlled rectifier has a cathode, an anode and a gate electrode, said voltage distributing means includes a capacitor and a resistor connected between said cathode and anode, said voltage breakdown means is connected between said anode and said gate electrode, and further including a protective diode connected between said gate electrode and said cathode and trigger means connected to said gate electrode.

14. The spark source of either claim 1 or 2 wherein said switching means is responsive to the voltage on said capacitor.

15. The spark source of claim 1 wherein said reactive means is an air core inductor and said capacitor includes a plurality of ceramic capacitors.

16. The spark source of any one of claims 1, 6, or 15 and further including resistance across said spark gap of value effective to allow essentially normal discharge of said capacitor in response to triggering of said discharge control means in the absence of sample material in said spark gap.

17. The spark source of claim 6 wherein said discharge control means is responsive to voltage on said capacitor.

18. The spark source of either claim 6 or 17 wherein each said controlled rectifier has a cathode, an anode and a gate electrode, said voltage distributing means includes a capacitor and a resistor connected between said cathode and anode, said voltage breakdown means is connected between said anode and said gate electrode, and further including a protective diode connected between said gate electrode and said cathode and trigger means connected to said gate electrode.

* * * * *